(12) United States Patent
Gordon, III et al.

(10) Patent No.: US 6,222,907 B1
(45) Date of Patent: Apr. 24, 2001

(54) IMAGE QUALITY OPTIMIZATION USING AN X-RAY MODEL BASED OPTIMIZATION

(75) Inventors: Clarence L. Gordon, III, Delafield; Gary F. Relihan, Nashotah, both of WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/351,469

(22) Filed: Jul. 12, 1999

(51) Int. Cl.[7] .............................. H05G 1/46; H05G 1/58
(52) U.S. Cl. .......................... 378/116; 378/62; 378/98.3
(58) Field of Search ..................... 378/62, 98.2, 98.3, 378/108, 110, 112, 116

(56) References Cited

U.S. PATENT DOCUMENTS 5,473,663 * 12/1995 Hsieh ................................ 378/207

6,005,916 * 12/1999 Johnson et al. .................. 378/87

OTHER PUBLICATIONS

Co-pending, commonly assigned U.S. Serial No. 09/351,755, entitled Exposure Management and Control System and Method, filed Jul. 12, 1999.

* cited by examiner

Primary Examiner—David V. Bruce
(74) Attorney, Agent, or Firm—Barbara Joan Haushalter; Christian G. Cabou; Phyllis Y. Price

(57) ABSTRACT

A model-based optimization is used to determine x-ray techniques for optimal image quality performance. The first step for achieving model-based optimization is to determine optimized techniques for a fixed spectral filter and focal spot to define a basic trajectory. The spectral filter and focal spot versus patient size are then optimized. The determined optimized techniques and the optimized spectral filter and focal spot versus patient size are used to create a functional trajectory which includes a Basic Trajectory Selector Table (indicating optimized spectral filter/focal spot) and the associated basic trajectories.

20 Claims, 5 Drawing Sheets

| PATIENT SIZE (mm) | FOCAL SPOT | SPECTRAL FILTER |
| --- | --- | --- |
| 0 | FS1 | SF1 |
| 50 | FS1 | SF3 |
| 100 | FS1 | SF3 |
| 150 | FS1 | SF3 |
| 200 | FS1 | SF3 |
| 250 | FS1 | SF3 |
| 300 | FS1 | SF2 |
| 350 | FS1 | SF2 |
| 400 | FS1 | SF2 |
| 450 | FS1 | SF2 |
| 500 | FS1 | SF2 |
| 550 | FS1 | SF1 |
| 600 | FS1 | SF1 |

FIG. 2

| FS1 THICK (mm) | SF1 kV | pw (ms) | pk_mA (mA) | det_dose (Gy) |
|---|---|---|---|---|
| 0 | 60 | 2 | 0.2 | 4.77E−09 |
| 50 | 72 | 4.3 | 0.2 | 4.51E−09 |
| 100 | 74 | 5 | 0.746 | 5.75E−09 |
| 150 | 82 | 5 | 2.62 | 8.49E−09 |
| 200 | 87 | 5 | 9.4 | 1.13E−08 |
| 250 | 94 | 5 | 30.6 | 1.49E−08 |
| 300 | 96 | 9.9 | 39.2 | 1.28E−08 |
| 350 | 104 | 12.5 | 29.4 | 5.23E−09 |
| 400 | 120 | 12.5 | 25.3 | 2.43E−09 |
| 450 | 120 | 12.5 | 27 | 8.98E−10 |
| 500 | 120 | 12.5 | 28.7 | 3.36E−10 |
| 550 | 120 | 12.5 | 30.5 | 1.27E−10 |
| 600 | 120 | 12.5 | 32.4 | 4.80E−11 |

| FS1 THICK (mm) | SF2 kV | pw (ms) | pk_mA (mA) | det_dose (Gy) |
|---|---|---|---|---|
| 0 | 62 | 2.2 | 0.2 | 3.45E−09 |
| 50 | 62 | 5 | 0.415 | 4.15E−09 |
| 100 | 66 | 5 | 1.5 | 5.29E−09 |
| 150 | 71 | 5 | 5.1 | 7.00E−09 |
| 200 | 75 | 5 | 17.2 | 8.89E−09 |
| 250 | 80 | 7.5 | 37 | 1.18E−08 |
| 300 | 111 | 12.5 | 36 | 2.12E−08 |
| 350 | 120 | 12.5 | 33.3 | 8.40E−09 |
| 400 | 120 | 12.5 | 33.3 | 2.88E−09 |
| 450 | 120 | 12.5 | 33.3 | 1.01E−09 |
| 500 | 120 | 12.5 | 33.3 | 3.55E−10 |
| 550 | 120 | 12.5 | 33.3 | 1.27E−10 |
| 600 | 120 | 12.5 | 33.3 | 4.55E−11 |

| FS1 THICK (mm) | SF3 kV | pw (ms) | pk_mA (mA) | det_dose (Gy) |
|---|---|---|---|---|
| 0 | 60 | 4.2 | 0.2 | 3.77E−09 |
| 50 | 61 | 5 | 0.694 | 4.44E−09 |
| 100 | 64 | 5 | 2.48 | 5.54E−09 |
| 150 | 66 | 5 | 8.89 | 6.52E−09 |
| 200 | 69 | 5 | 29.9 | 7.99E−09 |
| 250 | 74 | 12.5 | 36.1 | 1.05E−08 |
| 300 | 115 | 12.5 | 34.8 | 2.03−08 |
| 350 | 120 | 12.5 | 33.3 | 7.56E−09 |
| 400 | 120 | 12.5 | 33.3 | 2.61E−09 |
| 450 | 120 | 12.5 | 33.3 | 9.15E−10 |
| 500 | 120 | 12.5 | 33.3 | 3.24E−10 |
| 550 | 120 | 12.5 | 33.3 | 1.16E−10 |
| 600 | 120 | 12.5 | 33.3 | 4.20E−11 |

FIG. 3

IMAGE QUALITY OPTIMIZATION USING AN X-RAY MODEL BASED OPTIMIZATION

TECHNICAL FIELD

The present invention relates to the use of automatic x-ray technique control in fluoroscopic and record x-ray acquisition modes.

BACKGROUND ART

The x-ray techniques used to optimize image quality also strive to minimize exposure of the patient to x-ray radiation. These goals are independent of system limitations. Also, optimization varies with the type of medical exam being performed and the objective of the exam. These optimal techniques are required to successfully operate the x-ray system. The successful operation applies to a wide variety of clinical procedures and patient sizes performed on a x-ray system. The x-ray system can be a fluoroscopic or radiographic x-ray system. For example, vascular procedures typically require kVp settings in the 70 to 90 kVp range for imaging iodinated vessels. Conversely, gastrointestinal (GI) studies, which can be performed on the same system, prefer higher kVp for penetrating barium contrast media. In general, there are several parameters that are optimized versus patient size in order deliver exceptional image quality. These include focal spot size, x-ray beam quality through the use of spectral filtration, kVp, mA, exposure time, quantum noise level (i.e. detector entrance exposure per frame) and patient entrance exposure rate. Each of these parameters has an optimal setting, which is unique for each case.

Additionally, an order of complexity is added when trying to determine the optimal techniques allowed within the operational range of the x-ray system and/or local regulatory requirements. This is not necessarily the same technique as the true optimum independent of the x-ray system limitations.

It would be desirable to have a system and method for optimizing image quality. It would further be desirable to optimize image quality while meeting clinical imaging requirements. Finally, it would be desirable to optimize image quality while operating within the boundary of the system hardware and local regulatory requirements.

SUMMARY OF THE INVENTION

A x-ray technique for image quality optimization is provided. Optimal x-ray technique, which affects image quality, can be accurately predetermined to use for any application. A computer simulation of the x-ray system allows x-ray technique optimization to be performed quickly and efficiently. The optimization can be performed for multiple image quality parameters being weighted for importance to the current medical procedure.

A model-based optimization is used to determine x-ray techniques for optimal image quality performance. The first step for achieving model-based optimization is to determine optimized techniques for a fixed spectral filter and focal spot to define a basic trajectory. The spectral filter and focal spot versus patient size are then optimized. The determined optimized techniques and the optimized spectral filter and focal spot versus patient size are used to create a functional trajectory which includes a Basic Trajectory Selector Table (indicating optimized spectral filter/focal spot) and the associated basic trajectories.

Accordingly, the present invention provides image quality regulation and optimization. The model-based optimization for determining x-ray techniques can achieve optimal image quality for fluoroscopy or radioscopy applications.

BRIEF DESCRIPTION OF THE DRAWINGS

FIG. 2 shows a basic trajectory selector table;

FIG. 3 is a table showing a grouping of basic trajectories;

DETAILED DESCRIPTION OF THE PREFERRED EMBODIMENTS

Parameters that affect image quality include kVp, exposure time, image receptor entrance exposure or exposure rate, and focal spot. Parameters used to control the x-ray beam spectral quality also affect image quality. The optimization technique presented here requires the knowledge of many aspects of the clinical environment (procedure, patient size, etc.), as well as a complete description of the x-ray system and operating principles (x-ray photon physics) This knowledge is used to optimize the achievable techniques for each imaging situation that is performed on a given set of system hardware. The results of the optimization can be output in the form of a functional trajectory, i.e. optimized techniques versus patient size (thickness), to a x-ray exposure control system. This allows for consistent delivery of optimal image quality for any medical procedure, while obeying the constraints of the system and regulatory requirements. The trajectories can be generated and managed a priori though data files or running the optimization real-time when requested.

Figure 1:
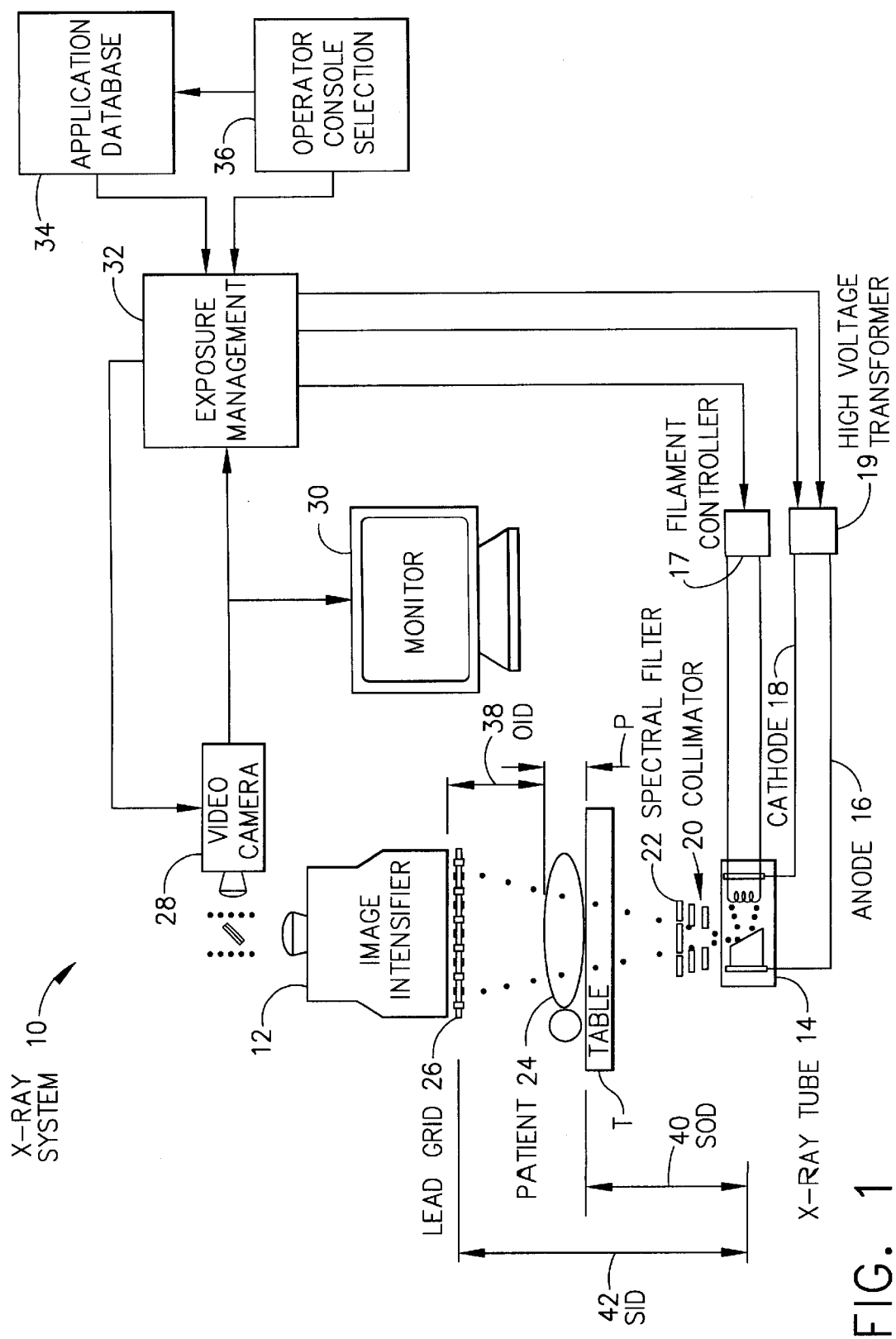
FIG. 1 is a block diagram of an x-ray system incorporating the present invention, having both fluoroscopy and radioscopy capabilities.

Referring now to the drawings, FIG. 1 illustrates a x-ray system 10 which has both fluoroscopy and radioscopy capabilities. The system 10 illustrated uses an analog detector, i.e., image intensifier 12 and video camera 28. However, the same model described herein can be applied to a system with a digital detector.

In FIG. 1, the image intensifier 12 receives x-rays produced by x-ray tube 14. The tube 14 has an associated anode 16 and cathode 18 structure. Also associated are a filament controller 17, and high voltage transformer 19. Collimator 20 collimates the x-rays. The x-rays may be filtered by spectral filter 22 before being transmitted through the object under study. The object under study, typically, is a human patient 24. Finally, the x-rays are received image intensifier 12 after passing through a lead anti-scatter grid 26. The image is transmitted through camera 28 and output to monitor 30. Various control and selection features are associated with exposure management block 32, application database 34 and operator console selection 36. Additional parameters relating to system geometry include source-to-image distance (SID) 42, source-to-object distance (SOD) 40, and object-to-image distance (OID) 38.

Present optimization schemes depend on simple algebraic rules or historical preferences for optimizing the technique settings described above. These are typically developed on one system type and are redeveloped or relearned when the goal of the procedure, the system configuration or the regulatory requirements change. This process, which can be based on trial and error, can be very lengthy and time consuming. These rules also tend to be simple functions or simple curve fits, sometimes missing needed optimization points in the more complex actual behavior.

A two-step method is provided herein to generate a x-ray technique trajectory. The method optimizes image quality for use in an exposure control system, hereafter referred to as a functional trajectory. Such an exposure control system is described and claimed in co-pending, commonly assigned patent application Ser. No. 09/351,755, totally incorporated herein by reference. The functional trajectory uses a x-ray spectral model based optimization platform. The optimized x-ray techniques (kVp, peak mA, exposure time, detector entrance exposure, x-ray beam quality [spectral filter], and focal spot) versus estimated patient size, are used in the exposure control system. Equivalent patient size, hereafter patient size, is a thickness of acrylic that has the same x-ray attenuation as the actual human anatomy of interest.

Typically, before each x-ray exposure sequence (group of any sequential images), the first thing to be determined is what focal spot and spectral filter is to be used for optimal image quality. From a previous exposure or patient anatomy information a starting patient size is known. The next exposure sequence will usually be performed in a relatively small patient size band around this operating point, so the optimal focal spot and spectral filter can be chosen using this information. In a particular trajectory implementation, the optimal spectral filter and focal spot can be represented in the functional trajectory. This can be represented in a table such as a Basic Trajectory Selector Table shown in the table of FIG. 2. In this particular table, the focal spot and spectral filter are assigned a coded value.

In addition to the Basic Trajectory Selector Table, the functional trajectory presented here contains a grouping of basic trajectories. This is shown in the Table of FIG. 3. When an exposure sequence (group of many sequential images) is begun, the exposure control system utilizes a set of optimized x-ray techniques for a specific spectral filter/focal spot combination. This is because the focal spot and spectral filter are typically in a fixed configuration during the sequence. A basic trajectory is a particular implementation of the source of the optimized techniques versus patient size for this particular focal spot/spectral filter combination. Even if the user moves to a patient size where this combination of focal spot/spectral filter is no longer optimal (as indicated in the Basic Trajectory Selector Table), the system is still able to deliver images with acceptable image quality. This is indicated in the current Basic Trajectory. However, the system is not able to deliver the optimal image quality that would be obtained if the optimal basic trajectory (i.e. the optimal focal spot/spectral filter combination) was used.

Having a method for the following is a key advantage of this optimization technique. The method includes using the knowledge on how to switch between optimal basic trajectories (i.e. focal spot/spectral filter). The method further includes maintaining the complete set of optimized techniques. This complete set is of the complete patient range for a particular spectral filter/focal spot choice.

Figure 4:
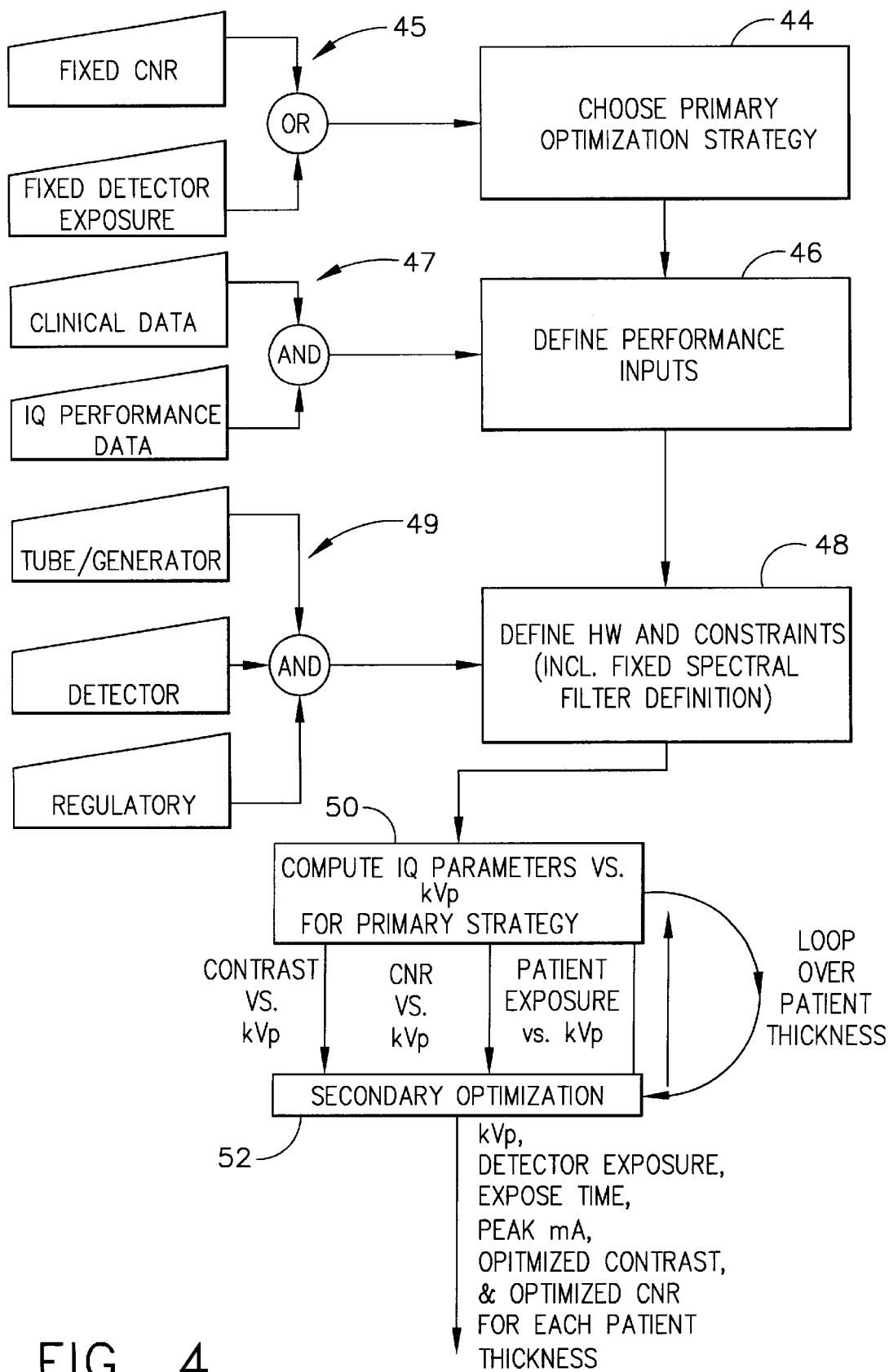
FIG. 4 is a flowchart block diagram illustrating features of a first step, to generate a basic trajectory, in the optimization processes.
Figure 5:
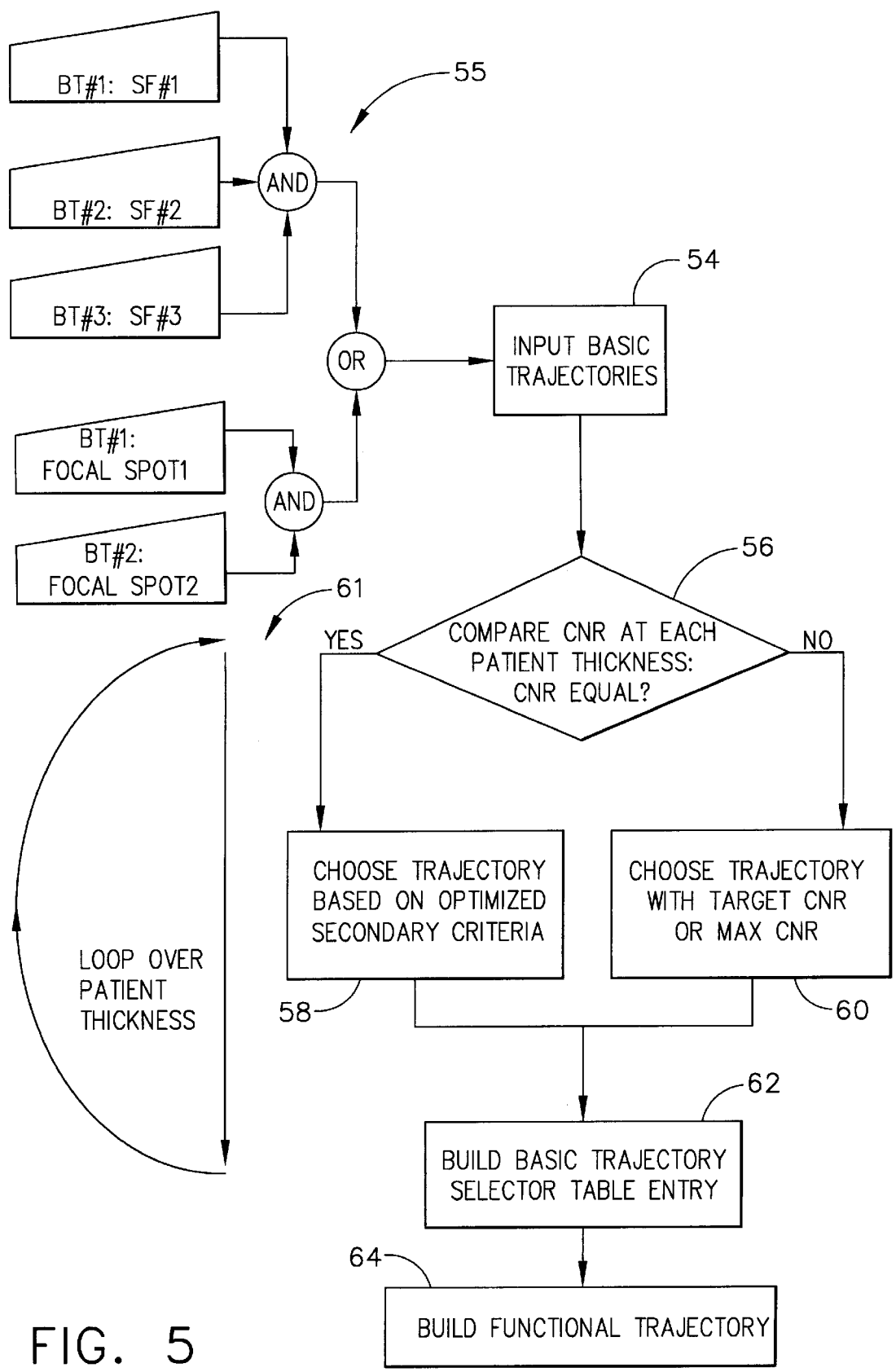
FIG. 5 is a flowchart block diagram illustrating features of a second step, to generate a functional trajectory, in the optimization processes.

Referring now to FIGS. 4 and 5, the two general steps in the optimization processes are illustrated in flowchart form. In FIG. 4, steps 44–52 are performed to determine the optimized techniques for a fixed spectral filter and focal spot. This format is known as a basic trajectory. In FIG. 5, steps 54–64 are performed to optimize the choice of the spectral filter and focal spot versus patient size. Steps 54–64 are also used to build a functional trajectory by combining the appropriate basic trajectories and creating the Basic Trajectory Selector Table of FIG. 2.

In FIG. 4, the function of block 44 is to choose the primary optimization strategy. The choice of the primary optimization strategy is the starting point of the optimization process. This strategy is the highest-level image quality goal of the optimization process. Any physical parameter that is modeled by the platform can be chosen, with the parameter typically versus patient size. Examples of parameters include fixed detector entrance exposure, fixed contrast to noise ratio (CNR) strategy, fixed contrast, fixed quantum noise properties, and fixed patient entrance dose, as indicated by reference number 45.

Each strategy will have a different advantage and can be tailored to match the needs of the clinical procedure. The ability to choose different strategies for each procedure type performed on the system is a benefit of this optimization method.

Continuing with FIG. 4, in step 46 of the optimization process, performance inputs are defined. The performance inputs comprise additional image quality goals and clinical requirements on the trajectory performance, indicated by reference number 47. First, image quality inputs can be data that specify the trajectory image quality performance. This includes, for example, the target value for the primary optimization strategy, a specification of the exposure time strategy vs. patient size, minimum contrast levels, contrast levels versus background dynamic range, maximum allowable patient entrance exposure (if different from the regulatory requirement), and maximum detector entrance exposure.

Second, clinical requirements describe the clinically relevant goals of the trajectory. This includes, for example, visualized object definition (thickness and material of object), exposure frame rate, patient thickness range, clinically relevant system geometry parameters (source-to-image distance vs. patient size, object-to-image distance vs. patient size, source-to-object distance), and maximum field-of-view at the detector.

In step 48, the system hardware and constraints are defined. This step highlights a key advantage of this model based optimization platform. That is, the ability to incorporate operational range of the system and regulatory requirements into the image quality optimization process. This ensures that the trajectories will provide the maximum performance that is allowed by the system hardware. The inputs that describe the hardware configuration, hardware constraints and regulatory requirements of the system include, for example, the elements indicated by reference number 49. These include operational range of the generator (min/max kVp, min/max exposure time, exposure rate). This further includes minimum and maximum tube peak mA limits (based on optimizing tube life). Also included is x-ray tube type (target angle and composition). X-ray tube material in x-ray beam path is also included. A description of the available focal spots and spectral filters is also a requirement. Detector properties (thickness of active layer and layer material) and anti-scatter grid properties are further requirements. Maximum patient entrance exposure rate regulations and absorbed organ dose limitations are also requirements.

Once all the inputs are defined, step 50 begins the optimization calculations for each patient thickness using a spectral based x-ray physic model. This is a level transfer model, from x-ray source to detected x-ray photons in the detector. This model includes calculations for radiation exposure in air, object contrast, and contrast-to-noise ratio.

The model uses the actual x-ray tube filtration, acrylic to simulate the patient, actual clinical object for contrast, and actual detector properties to compute the level and noise of the detected x-rays. This model can include items such as quantum noise or contrast reduction due to detector/system modulation transfer function (MTF), detected quantum efficiency (DQE) of the detector, half value layer (HVL) calculations, etc. This model needs to accommodate the entire physical behavior that is relevant to the optimization process at hand.

First, in step 50, the required average mA to meet the primary optimization strategy value is determined. Also, any limits on average mA are incorporated. Typically, many constraints can be formulated into average mA limits versus kVp. The regulatory limitation on patient entrance exposure rate and the average power limit of the x-ray tube is easily transformed to the average mA limit. If desired, the ability to reach the performance specified by the primary optimization criteria can be limited to accommodate these constraints of the system.

Second, in step 50, an exposure time strategy and any peak mA constraints are applied. These determine the final choice of peak mA and exposure time at this patient size and kVp operating point. For example, the x-ray tube, to keep from damaging the target surface, also has a constraint on the peak mA values that can be used for a given exposure at a given kVp. In addition, another advantage of this technique is the ability to incorporate many different strategies into the same tool. The case of exposure time is a good example. That is, many exposure time strategies could be incorporated. These include, for example: fixed exposure time (overridden by constraints), variable exposure time versus kVp, variable exposure time versus patient size, etc.

For the output of step 50, the contrast, contrast-to-noise ratio, and patient entrance exposure are computed. These are the optimal or the maximum allowed value at each kVp. This is based on either the optimization goal or a constraint limit. These are computed in the specified hardware range for every patient thickness.

The final step 52 in the basic trajectory takes the data from block 50 to determine the optimal kVp point for the patient size under consideration. This step is performed differently depending on the primary optimization strategy. However, it typically uses secondary optimization criteria. This can be, for example, minimum patient entrance exposure or maximum contrast. Step 52 still maintains the primary goal, however, to choose the optimal kVp for each patient size (and associated peak inA, exposure time, and detector entrance exposure).

These optimal technique factors indexed versus patient size are chosen for a fixed spectral filter and focal spot size. These optimal technique factors are known as the basic trajectory. Three grouped basic trajectories are shown in the table of FIG. 3.

Referring now to FIG. 5, the steps for achieving functional trajectory optimization are illustrated. Step 54, inputting basic trajectories, is the first step to build a functional trajectory. The number of basic trajectories used in this step depends on the goal of the functional trajectory. Each basic trajectory is input with its associated spectral filter and its associated focal spot, as indicated by reference number 55. By way of example, for fluoro, which is typically operated with a small focal spot, there will be N input basic trajectories. That is, one for each of N available spectral filters. For cardiac, it is probably best to use the minimal spectral filtration fixed for all patient sizes. However, the focal spot can vary with patient size.

At decision block 56, typical figures of merit are used to choose optimal basic trajectory, among spectral filter/focal spot combinations under consideration. For a specific patient thickness, either the contrast or the contrast-to-noise ratio (CNR) is used. Optionally, any other relevant image quality parameter could be used. The values of contrast or CNR in each basic trajectory at the same patient thickness are examined. The first decision is to determine if the values under investigation between each basic trajectory are equal. This drives what is done in the next step to choose the optimal basic trajectory.

In steps 58 and 60, optimal basic trajectory is chosen. If the CNR values are different in the basic trajectories at the patient size under consideration, the optimal basic trajectory choice is affected. For example, it may be first based on choosing the value that is at the maximum CNR value. Conversely, the CNR values may be equal in the basic trajectories at the patient size under consideration. Then, the optimal basic trajectory choice will be made with secondary optimization criteria. This could be the basic trajectory with the minimum patient entrance exposure or maximum contrast. Alternatively, it could be any image quality parameter.

After the optimal basic trajectory is chosen (and hence the optimal spectral filter or focal spot) at each patient size, step 62 occurs. In step 62, the Basic Trajectory Selector Table such as the example table of FIG. 2, is generated for inclusion in the functional trajectory. The table will actually indicate which focal spot or spectral filter is to be used versus patient size. The loop over the patient thickness, indicated by reference number 61, loops steps 56 to 62.

Finally, in step 64, the generation of the functional trajectory is achieved. The x-ray technique optimization technique will perform this task. It then delivers the functional trajectories to be used by the exposure control system on the x-ray product. This step can include creating a data header, linking it with the Basic Trajectory Selector Table generated at step 62, and then organizing associated basic trajectories.

Those skilled in the art will recognize that this process is just one particular implementation that is most easily applied to generating trajectories a priori. For a real time system, this process would be done by request for a specific patient size on an as needed basis.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A model based optimization method for determining x-ray techniques for optimal image quality performance of a x-ray system, the method comprising the steps of:

determining optimized techniques for a fixed spectral filter and focal spot to define a basic trajectory;

optimizing the spectral filter and focal spot versus patient size; and combining the determined optimized techniques for a fixed spectral filter and focal spot with the optimized spectral filter and focal spot versus patient size, to create a functional trajectory.

2. A method as claimed in claim 1 wherein the step of determining optimized techniques comprises the steps of:
 selecting a primary optimization strategy to match needs of a clinical procedure; and
 defining performance inputs based on the selected primary optimization strategy.

3. A method as claimed in claim 2 wherein the step of determining optimized techniques further comprises the step of computing image quality parameters versus potential voltage for the primary optimization strategy.

4. A method as claimed in claim 3 wherein the step of computing further comprises the steps of:
 determining a required average current to meet the primary optimization strategy; and
 incorporating into the computation any limits on average current.

5. A method as claimed in claim 4 wherein the step of computing further comprises the step of applying an exposure time strategy and any peak current constraints to a determination of peak current and exposure time at a given patient size and operating point.

6. A method as claimed in claim 5 wherein the step of computing further comprises the step of computing optimal or maximum allowed values for contrast, contrast-to-noise ratio and patient entrance exposure for every patient thickness in a specified hardware range.

7. A method as claimed in claim 5 wherein the step of determining optimized techniques further comprises the step of determining an optimal potential voltage point for a given patient size.

8. A method as claimed in claim 7 further comprising the step of using a secondary optimization criteria to determine the optimal potential voltage point for a given patient size.

9. A method as claimed in claim 2 wherein the step of defining performance inputs comprises the step of defining performance inputs having image quality goals and clinical requirements on a trajectory performance.

10. A method as claimed in claim 9 wherein the image quality goals specify trajectory image quality performance.

11. A method as claimed in claim 9 wherein the clinical requirements describe clinically relevant goals of the trajectory.

12. A method as claimed in claim 1 wherein the step of determining optimized techniques further comprises the step of incorporating operational range of the x-ray system and regulatory requirements into the optimized techniques determination.

13. A method as claimed in claim 1 wherein the step of optimizing the spectral filter and focal spot versus patient size comprises the steps of:
 inputting a basic trajectory for each spectral filter available in the x-ray system;
 comparing contrast-to-noise ratio at each patient thickness using the inputted basic trajectories;
 selecting an optimal basic trajectory based on the contrast-to-noise ratio comparison;
 generating a basic trajectory selector table using the optimal basic trajectory to indicate proper focal spot or spectral filter to be used versus patient size; and
 generating a functional trajectory containing a basic trajectory selector table and the inputted basic trajectories for use by an exposure control system on the x-ray system.

14. A method as claimed in claim 1 wherein the functional trajectory comprises:
 a basic trajectory selector table; and
 associated basic trajectories.

15. A model based optimization system for determining x-ray techniques for optimal image quality performance of an x-ray system, the system comprising:
 optimized techniques determined for a fixed spectral filter and focal spot to define a basic trajectory;
 optimized spectral filter and focal spot versus patient size; and
 means for combining the determined optimized techniques for a fixed spectral filter and focal spot with the optimized spectral filter and focal spot versus patient size, to create a functional trajectory.

16. A system as claimed in claim 15 wherein the optimized techniques comprise:
 a primary optimization strategy selected to match needs of a clinical procedure;
 performance inputs based on the selected primary optimization strategy;
 means for computing image quality parameters versus potential voltage for the primary optimization strategy.

17. A system as claimed in claim 16 wherein the performance inputs comprise performance inputs having image quality goals and clinical requirements on a trajectory performance.

18. A system as claimed in claim 17 wherein the image quality goals specify trajectory image quality performance and the clinical requirements describe clinically relevant goals of the trajectory.

19. A system as claimed in claim 15 wherein the optimized techniques further comprise means for incorporating operational range of the x-ray system and regulatory requirements into the optimized techniques determination.

20. A system as claimed in claim 15 wherein the optimized spectral filter and focal spot versus patient size comprise:
 a basic trajectory input for each spectral filter available in the x-ray system;
 means for comparing contrast-to-noise ratio at each patient thickness using the inputted basic trajectories;
 an optimal basic trajectory selected based on the contrast-to-noise ratio comparison;
 a basic trajectory selector table generated using the optimal basic trajectory to indicate proper focal spot or spectral filter to be used versus patient size; and
 a functional trajectory containing a basic trajectory selector table and the inputted basic trajectories for use by an exposure control system on the x-ray system.

* * * * *